United States Patent [19]

Liczwek et al.

[11] Patent Number: 5,006,259
[45] Date of Patent: Apr. 9, 1991

[54] PROCESS AND MEANS FOR USE OF ANAPHYLATOXIN ADSORBENTS

[75] Inventors: Deborah L. Liczwek, West Chester, Pa.; Erwin A. Vogler, New Hill, N.C.

[73] Assignee: E. I. Du Pont de Nemours and Company, Wilmington, Del.

[21] Appl. No.: 315,966

[22] Filed: Mar. 2, 1989

Related U.S. Application Data

[62] Division of Ser. No. 171,027, Mar. 21, 1988, abandoned.

[51] Int. Cl.⁵ .................. B01D 15/00; A61K 31/74; A61K 31/745
[52] U.S. Cl. .................................. 210/692; 424/78; 424/83; 523/112
[58] Field of Search .................. 424/78, 83, 101; 523/112; 210/692

[56] References Cited

U.S. PATENT DOCUMENTS

| | | | |
|---|---|---|---|
| 4,132,682 | 1/1979 | Seito et al. | 526/247 |
| 4,138,373 | 2/1979 | Ukihashi et al. | 526/247 |
| 4,138,426 | 2/1979 | England | 526/247 |
| 4,267,364 | 5/1981 | Grot et al. | 521/27 |
| 4,610,815 | 9/1986 | Wissler | 435/68 |
| 4,831,118 | 5/1989 | Zimmerman et al. | 424/101 |

FOREIGN PATENT DOCUMENTS

62-261368 11/1987 Japan.

OTHER PUBLICATIONS

Shimizu, "Functional Polymers for Separation", 1984 High Polymers Japan, vol. 33, #11, pp. 843-848.
Masashi, Suzuki, "Recent Advances in Hemodialysis", 1981 Japanese Journal of Artificial Organs, vol. 16, #3, pp. 1180-1184.
Takehisa, "Development of Anaphylatoxin Scavenging Device", Japanese Journal of Artifical Organs, vol. 17, #2, pp. 515-520 (1988).

Primary Examiner—Lester L. Lee
Assistant Examiner—Carmen B. Pili-Cuttis

[57] ABSTRACT

Anaphylatoxin adsorbing perfluorinated tetrafluoroethylene copolymer containing acid or selected acid derivative functionality, and process and means for the use thereof.

5 Claims, 1 Drawing Sheet

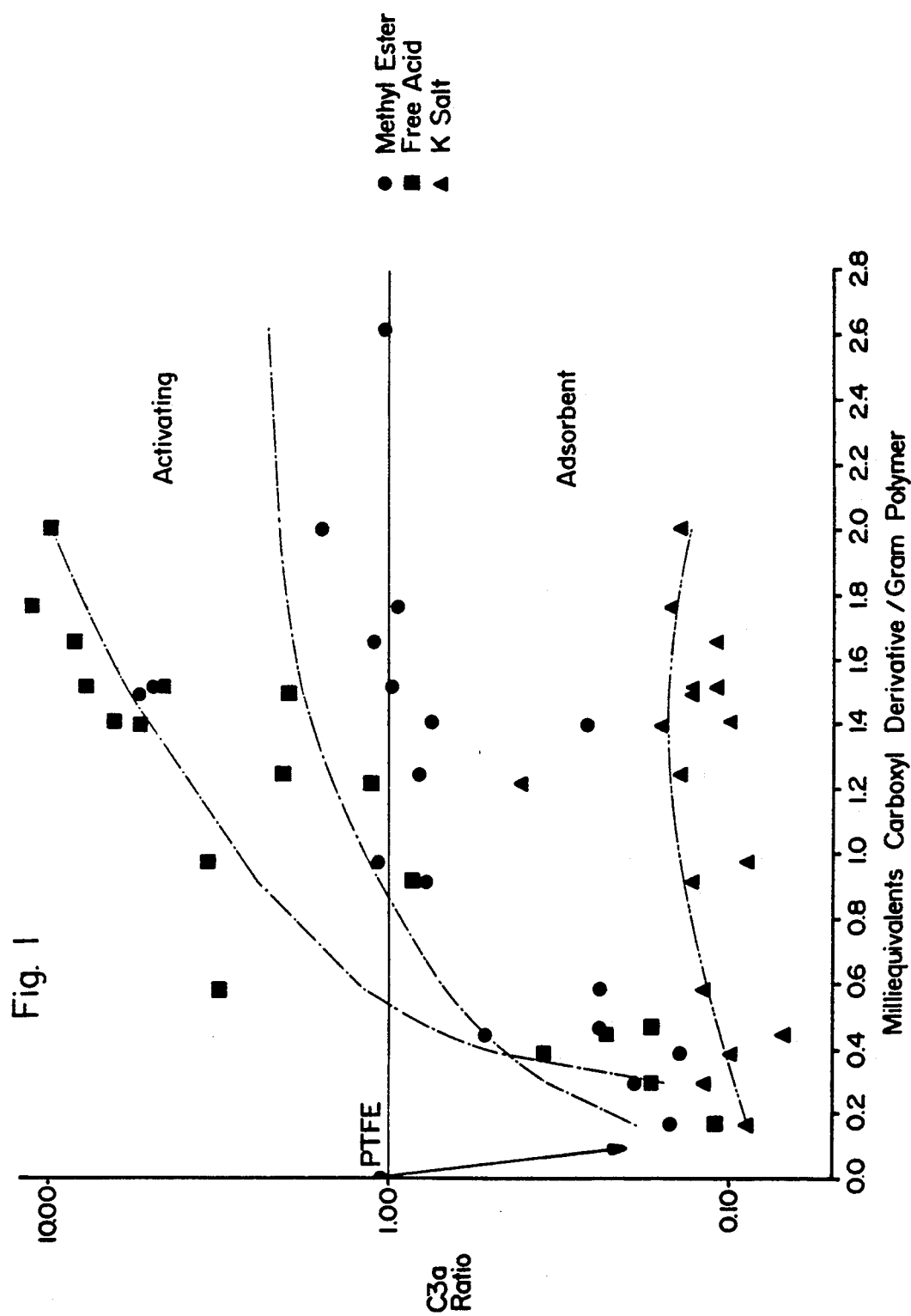

1

PROCESS AND MEANS FOR USE OF ANAPHYLATOXIN ADSORBENTS

CROSS-REFERENCE TO RELATED APPLICATION

This is a division of Application No. 07/171,027 filed Mar. 21, 1988 and now abandoned.

BACKGROUND

Blood contains a complement system which functions primarily as an effector mechanism in the immune defense against microbial infection. When activated, as for example by antigen-antibody complexes or by substances of microbial origin, the complement system produces substances termed anaphylatoxins. Anaphylatoxins are responsible for immune responses such as cell lysis, chemotraction of phagocytic cells, and facilitation of the uptake and destruction of foreign particles by phagocytic cells.

The blood complement system consists of a set of nine distinct plasma proteins designated $C_1$ through $C_9$. Upon activation as described above, physiologically active peptides are generated which are part of the anaphylactic response, and hence, are called anaphylatoxins. These activated derivatives of the nine complement plasma proteins are designated $C3_a$, $C4_a$, etc.

There are instances when unwanted activation of the complement system occurs. For example, when blood flow is diverted from the human body for therapeutic processing or for bypass purposes and is then returned to the human body. Contact with artificial surfaces such as are found in extracorporeal blood circuits frequently activates the complement system. Plastic surfaces such as nylon, or surfaces of sepharose have poor compatibility with blood and activate the complement system. Unwanted clinical complications can arise if activated blood is returned to the body. Thus, clinical procedures such as hemodialysis, cardiopulmonary bypass or leukapheresis filtration are rendered more difficult to perform by such activation. Unfortunately, also, many materials used in blood contact applications such as cellulosic dialysis membranes and polyester transfusion filters activate the blood complement system resulting in adverse clinical symptoms.

There is a need for materials which do not activate blood, and which serve as adsorbents for the anaphylatoxins, so that the anaphylatoxins formed when blood passes through the extracorporeal devices, can be removed before the blood reenters the human body.

SUMMARY OF INVENTION

The materials of this invention adsorb anaphylatoxins and do not activate blood. They are tetrafluoroethylene copolymers consisting essentially of recurring units of tetrafluoroethylene and recurring units of one or more of the following comonomers selected from $$CF_2=CF-(OB-)-(OCF_2CF_2)_x-COOR,$$

wherein B is perfluoro alkylene of 2-4 carbon atoms (including branched alkylene), x is a cardinal number of 0-4, and R is hydrogen, alkyl of 1 to 12 carbon atoms, or a metal cation, preferably a Group I or II cation and most preferably sodium or potassium.

DETAILED DESCRIPTION OF THE INVENTION

Specific preferred comonomers within the general class include:

(i) $CF_2=CF-O-CF_2\underset{\underset{CF_3}{|}}{CF}-O-CF_2-CF_2-COOR,$ (ii) $CF_2=CF-O-(CF_2)_4-COOR,$
(iii) $CF_2=CF-O-(CF_2)_3-COOR,$
(iv) $CF_2=CF-O-(CF_2)_2COOR,$ and the like.

The amount of comonomer present will be an amount sufficient to impart anaphylatoxin adsorbtion to the copolymer. Preferably, the amount, for free acid comonomers, i.e., comonomers where R is hydrogen, will be an amount sufficient to provide between 0.1 and 1.0 milliequivalent of free acid groups per gram of copolymer. Preferably the amount, for ester comonomers, i.e., comonomers where R is alkyl, will be an amount sufficient to provide between 0.1 and 1.5 milliequivalents of ester groups per gram of copolymer. Preferably the amount, for metal salts, i.e., comonomers where R is a metal cation, will be an amount sufficient to provide between 0.1 and 2 milliequivalents of COO-metal group per gram of copolymers. Metals include sodium, potassium, calcium magnesium, and the like.

Preparation of the copolymers of this invention can be by any of the known methods for polymerizing tetrafluoroethylene with acid perfluorinated comonomers, as for example as shown in U.S. Pat. No. 4,267,364. All polymerizations were carried out with perfluorocarboxylate comonomers in the methyl ester form. Corresponding potassium salt forms were prepared by hydrolysis in 10% aqueous KOH. Samples were heated to 100° C. for 18 hours. Conversion was confirmed by x-ray fluorescence spectrometry. Perfluorocarboxylic acids forms were prepared by acid hydrolysis of K salt forms in concentrated nitric acid. Samples were heated to 100° C. for 18 hours in 10% aqueous $HNO_3$ with 30% dimethylsulfoxide (DMSO). Hexyl and butyl esters were prepared from free acids by refluxing in pure hexanol or butanol, respectively, for 18 hours. Water was removed by distillation and polymer samples recovered by filtration.

The copolymers adsorb anaphylatoxins from blood on contact, which makes the copolymers useful in removing anaphylatoxins from anaphylatoxin-contaminated blood before the blood is returned to the human body. This can most easily be carried out by placing the copolymer in a packing tube or column or in a flat bed and passing the contaminated blood through the tube or column or over the bed. More specifically, the utility of the copolymer as a blood treating agent will suggest to one skilled in the art a variety of means through which this utility can be manifested. For example, the copolymer can comprise an integral part of an extracorporeal therapy column or, if desired, it can be applied as a coating, from a dispersion or solution, to a membrane, for example, a semipermeable membrane. As is well known, such membranes can be in the form of either a flat sheet membrane or a hollow fiber membrane.

The copolymers can contain other recurring comonomer units that do not substantially affect the adsorption of anaphylatoxin. These are usually perfluorinated comonomers. Such comonomers include hexafluoropropylene, or organic comonomers containing sulfonyl fluoride or salts, such as $CF_2=CF-(OB)-(OCF_2CF_2-xSO_2F$ or the $SO_3$/metal salt analogs thereof. The amount of the sulfur containing comonomer is usually present in an amount sufficient to give 0.1-0.9 milliequivalents sulfonyl group per equivalent of copolymer.

EXAMPLES

In the examples, blood complement activation was determined using a commercial radioimmunoassay kit (Upjohn Diagnostics) which measured C3a concentrations in human plasma which had contacted test materials. The test was performed as set forth in product directions and further described in "Measurement of Anaphylatoxins: An Index of Activation of Complement Cascades" by Satoh et al, in Biotechniques, June/July 1983, page 91. Plasma not brought into contact with test materials served as negative controls and typically yielded less than 10 micrograms ($\mu$g) C3a/ml plasma. Sepharose served as a positive control and typically yielded tenfold greater C3a levels than negative control. Between 100-200 mg of polymer powder was added to 1 ml of plasma in each test and results reported as a ratio (C3a Ratio) of test response to negative control:

$R_{C3a} = \mu g$ C3a test sample$/(\mu g$ C3a negative control).

Thus, activating materials yield $R_{C3a} > 1$ and blood inert materials give $R_{hd\ C3a} = 1$. Adsorption of C3a from plasma to levels below background are indicated by $R_{C3a} < 1$.

FIG. 1 plots complement activation results ($R_{C3a}$) as a function of acid-group concentration (in milliequivalents/gram polymer, mEq/g; note logarithmic ordinate scale). Polytetrafluoroethylene homopolymer (PTFE) was selected as a fluoropolymer with no acid copolymer content and was essentially blood inert, yielding $R_{C3a}$ near unity (PTFE = 0 mEq/g acid group, see horizontal line in the figure). At low carboxyl concentrations, free acid, ester, and salt forms were efficient adsorbents of C3a. In excess of 1 mEq/g, free acids were strongly activating whereas ester forms were nearly inert. Potassium salt forms were adsorbent at all compositions. Tables I-III collect results and copolymer identities.

Table IV collects complement activation results of hexyl and butyl ester forms of selected copolymer compositions. Table V summarizes results for calcium salt forms. Alternate ester and salt forms are active C3a adsorbents. Table VI lists complement activation of perfluorocarboxylate ter-polymers containing a perfluorosulfonyl monomer. Presence of recurring sulfonyl fluoride units does not substantially affect C3a adsorbent properties.

TABLE I

Complement Activation of Perfluorocarboxylic Acid Copolymers of Tetrafluoroethylene

| mEq/gram Perfluorocarboxylate | Comonomer Identity | $C3_a$ Ratio | Standard Deviation |
|---|---|---|---|
| 0.17 | MPOO | 0.11 | 0.82 |
| 0.30 | MPOO | 0.17 | 0.03 |
| 0.39 | MPOO | 0.35 | 0.10 |
| 0.45 | MPOO | 0.23 | 0.07 |
| 0.47 | EVE | 0.17 | 0.03 |
| 0.59 | MPOH | 3.12 | 0.73 |
| 0.92 | EVE | 0.05 | 0.09 |

TABLE I-continued

Complement Activation of Perfluorocarboxylic Acid Copolymers of Tetrafluoroethylene

| mEq/gram Perfluorocarboxylate | Comonomer Identity | $C3_a$ Ratio | Standard Deviation |
|---|---|---|---|
| 0.98 | MPOH | 3.36 | 0.49 |
| 1.22 | MAEVE | 1.12 | 0.15 |
| 1.25 | MAEVE | 2.03 | 0.25 |
| 1.40 | MPOH | 5.35 | 0.48 |
| 1.41 | MAEVE | 6.39 | 0.94 |
| 1.50 | MAEVE | 1.95 | 0.37 |
| 1.52 | MAEVE | 7.70 | 1.02 |
| 1.52 | MAEVE | 4.58 | 1.10 |
| 1.66 | MAEVE | 8.32 | 0.71 |
| 1.77 | MAEVE | 11.16 | 2.14 |
| 2.01 | MPOH | 9.74 | 2.30 | mEq/gram = milliequivalents carboxylate moiety/gram polymer
Mean values and standard deviations of duplicate trials.
MPOO = $CF_2=CF-O-(CF_2)_4-COOH$,
MPOH = $CF_2=CF-O-(CF_2)_3-COOH$,
MAEVE = $CF_2=CF-O-(CF_2)_2-COOH$,
EVE = $CF_2=CF-O-CF_2-CF(CF_3)-O-(CF_2)_2-COOH$.

TABLE II

Complement Activation of Methyl Perfluorocarboxylate Copolymers of Tetrafluoroethylene

| mEq/gram Carboxylate | Comonomer Identity | $C3_a$ Ratio | Standard Deviation |
|---|---|---|---|
| 0.17 | MPOO | 0.15 | 0.11 |
| 0.30 | MPOO | 0.19 | 0.09 |
| 0.39 | MPOO | 0.14 | 0.11 |
| 0.45 | MPOO | 0.52 | 0.07 |
| 0.47 | EVE | 0.24 | 0.32 |
| 0.59 | MPOH | 0.24 | 0.17 |
| 0.92 | EVE | 0.77 | 0.17 |
| 0.98 | MPOH | 1.07 | 0.50 |
| 1.25 | MAEVE | 0.81 | 0.31 |
| 1.40 | MPOH | 0.26 | 0.04 |
| 1.41 | MAEVE | 0.75 | 0.09 |
| 1.50 | MAEVE | 5.37 | 0.67 |
| 1.52 | MAEVE | 0.97 | 0.18 |
| 1.52 | MAEVE | 4.91 | 1.04 |
| 1.66 | MAEVE | 1.10 | 0.36 |
| 1.77 | MAEVE | 0.93 | 0.31 |
| 2.01 | MPOH | 1.57 | 0.50 |
| 2.62 | MPOH | 1.02 | 0.20 | mEq/gram = milliequivalents carboxylate moiety/gram polymer.
Mean values and standard deviations of duplicate trials.
MPOO = $CF_2=CF-O-(CF_2)_4-COOCH_3$,
MPOH = $CF_2-CF-O-(CF_2)_3-COOCH_3$,
MAEVE = $CF_2=CF-O-(CF_2)_2-COOCH_3$,
EVE = $CF_2=CF-O-CF_2-CF(CF_3)-O-(CF_2)_2-COOCH_3$.

TABLE III

Complement Activation of Potassium Perfluorocarboxylate Copolymers of Tetrafluoroethylene

| mEq/Carboxyl per gram | Comonomer Identity | $C3_a$ Ratio | Standard Deviation |
|---|---|---|---|
| 0.17 | MPOO | 0.09 | 0.02 |
| 0.30 | MPOO | 0.12 | 0.06 |
| 0.39 | MPOO | 0.10 | 0.05 |
| 0.45 | MPOO | 0.07 | 0.04 |
| 0.59 | MPOH | 0.12 | 0.07 |
| 0.92 | EVE | 0.13 | 0.12 |
| 0.98 | MPOH | 0.09 | 0.03 |
| 1.22 | MAEVE | 0.41 | 0.06 |
| 1.25 | MAEVE | 0.14 | 0.03 |
| 1.40 | MPOH | 0.16 | 0.04 |
| 1.41 | MAEVE | 0.10 | 0.07 |
| 1.50 | MAEVE | 0.13 | 0.07 |
| 1.52 | MAEVE | 0.11 | 0.02 |
| 1.52 | MAEVE | 0.13 | 0.03 |
| 1.66 | MAEVE | 0.11 | 0.07 |
| 1.77 | MAEVE | 0.15 | 0.96 |

TABLE III-continued

Complement Activation of Potassium Perfluorocarboxylate Copolymers of Tetrafluoroethylene

| mEq/Carboxyl per gram | Comonomer Identity | $C3_a$ Ratio | Standard Deviation |
|---|---|---|---|
| 2.01 | MPOH | 0.14 | 0.01 | mEq/gram = milliequivalents carboxylate moiety/gram polymer
Mean values and standard deviations of duplicate trials.
MPOO = $CF_2=CF-O-(CF_2)_4-COOK$,
MPOH = $CF_2=CF-O-(CF_2)_3-COOK$,
MAEVE = $CF_2=CF-O-(CF_2)_2-COOK$,
EVE = $CF_2=CF-O-CF_2-CF(CF_3)-O-(CF_2)_2-COOK$.

TABLE IV

Complement Activation of Butyl and Hexyl Perfluorocarboxylate Copolymers of Tetrafluoroethylene

| mEq/gram Carboxylate | Comonomer Identity | Ester Type | $C3_a$ Ratio | Standard Deviation |
|---|---|---|---|---|
| 1.40 | MPOH | Butyl | 0.76 | 0.11 |
| 1.40 | MPOH | Hexyl | 0.89 | 0.11 |
| 1.52 | MAEVE | Butyl | 0.70 | 0.11 |
| 1.52 | MAEVE | Hexyl | 0.83 | 0.12 | mEq/gram = milliequivalents carboxylate moiety/gram polymer.
Mean values and standard deviations of duplicate trials.
MPOH = $CF_2=CF-O-(CF_2)_3-COOR$,
MAEVE = $CF_2=CF-O-(CF_2)_2-COOR$,
R = butyl or hexyl.

TABLE V

Complement Activation of Calcium Perfluorocarboxylate Copolymers of Tetrafluoroethylene

| mEq/gram Carboxylate | Comonomer Identity | $C3_a$ Ratio | Standard Deviation |
|---|---|---|---|
| 1.77 | MAEVE | 0.33 | 0.09 |
| 0.39 | MPOO | 0.20 | 0.07 |
| 0.98 | MPOH | 0.29 | 0.11 | mEq/gram milliequivalents carboxylate moiety/gram polymer.
Mean values and standard deviations of duplicate trials.
MPOO = $CF_2=CF-O-(CF_2)_4-COOC_a$,
MPOH = $CF_2=CF-O-(CF_2)_3-COOC_a$,
MAEVE = $CF_2=CF-O-(CF_2)_2-COOC_a$.

The results of Tables I–III are depicted graphically in FIG. 1.

TABLE VI

Complement Activation of Methyl Perfluorocarboxylate Ter-polymers

| m/Eq/gram Perfluoro carboxylate | Comonomer Identity | mEq/gram Sulfonyl Fluoride | C3a Ratio | Standard Deviation |
|---|---|---|---|---|
| 0.25 | MPOO | 0.64 | 0.76 | 0.06 |
| 0.27 | MPOO | 0.39 | 0.35 | 0.01 |
| 0.33 | MPOO | 0.49 | 0.38 | 0.14 |
| 0.50 | EVE | 0.42 | 0.30 | 0.30 |
| 0.52 | MPOH | 0.24 | 0.26 | 0.14 |
| 0.59 | MPOH | 0.43 | 0.36 | 0.32 |
| 0.77 | MPOH | 0.38 | 0.57 | 0.23 |
| 1.05 | MPOO | 0.56 | 2.74 | 0.34 | mEq/gram = milliequivalents carboxylate moiety/gram polymer.
Sulfonyl Fluoride monomer = $[CF_2=CF-O-CF_2-CF(CF_3)-O-(CF_2)_2-SO_2F]$.
Mean values and standard deviations of duplicate trials.
MPOO = $CF_2=CF-O-(CF_2)_4-COOCH_3$,
MPOH = $CF_2=CF-O-(CF_2)_3-COOCH_3$,
EVE = $CF_2=CF-O-CF_2-CF(CF_3)-O-(CF_2)_2-COOCH_3$.

I claim:

1. Process for adsorbing anaphylatoxins from anaphylatoxin-contaminated blood, which process comprises contacting the contaminated blood with at least one tetrafluoroethylene copolymer consisting essentially of recurring units of
   (a) tetrafluoroethylene, and
   (b) recurring units of one or more comonomers of the structure $CF_2=CF-(OB)-(OCF_2CF_2)_xCOOR$,
   wherein B is perfluoro alkylene of 2–4 carbon atoms, x is a cardinal number of 0–4, and R is hydrogen, alkyl of 1 to 12 carbon atoms, or a metal cation,
   wherein the units of component (b) are present in an amount sufficient to cause the copolymer to adsorb anaphylatoxins from blood.

2. The process of claim 1 wherein component (b) is selected from the class consisting of $$CF_2=CF-O-CF_2-\underset{\underset{CF_3}{|}}{C}F-O-CF_2-CF_2-COOR, \quad (i)$$

(ii) $CF_2=CF-O-(CF_2)_4-COOR$, (iii) $CF_2=CF-O-(CF_2)_3-COOR$, and (iv) $CF_2=CF-O-(CF_2)_2COOR$.

3. The process of claim 2 wherein the amount of any acid comonomer is 0.1 to 1.0 milliequivalent of free acid groups per gram of copolymer.

4. The process of claim 2 wherein the amount of any ester comonomer is 0.1 to 1.5 milliequivalents of ester groups per gram of copolymer.

5. The process of claim 2 wherein the amount of any metal salt comonomer is 0.1 to 2.0 milliequivalents of COO-metal groups per gram of copolymer.

* * * * *

UNITED STATES PATENT AND TRADEMARK OFFICE
CERTIFICATE OF CORRECTION

PATENT NO. : 5,006,259

DATED : April 9, 1991

INVENTOR(S) : Liczwek, et al.

It is certified that error appears in the above-identified patent and that said Letters Patent is hereby corrected as shown below:

Col. 6, claim 1, line 2, after "-contaminated blood" insert --without blood complement activation--.

Signed and Sealed this

Twenty-second Day of September, 1992

Attest:

DOUGLAS B. COMER

Attesting Officer

Acting Commissioner of Patents and Trademarks